(12) United States Patent
Chen et al.

(10) Patent No.: US 8,247,689 B2
(45) Date of Patent: Aug. 21, 2012

(54) RUTHENIUM COMPLEX AND PHOTOELECTRIC COMPONENT USING THE SAME

(75) Inventors: Ching-Lin Chen, Taoyuan Hsien (TW); Ta-Chung Yin, Taoyuan Hsien (TW); Der-Gun Chou, Taoyuan Hsien (TW)

(73) Assignee: Everlight USA, Inc., Pineville, NC (US)

( * ) Notice: Subject to any disclaimer, the term of this patent is extended or adjusted under 35 U.S.C. 154(b) by 653 days.

(21) Appl. No.: 12/318,207

(22) Filed: Dec. 23, 2008

(65) Prior Publication Data

US 2010/0084018 A1     Apr. 8, 2010

(30) Foreign Application Priority Data

Oct. 6, 2008     (CN) .......................... 2008 1 0161990

(51) Int. Cl.
*H01L 31/042*     (2006.01)
(52) U.S. Cl. .................... 136/265; 136/256; 556/136
(58) Field of Classification Search .................. 136/256, 136/263; 556/136
See application file for complete search history.

(56) References Cited

U.S. PATENT DOCUMENTS

| | | | | |
|---|---|---|---|---|
| 6,586,670 B2 * | 7/2003 | Yoshikawa | .................... | 136/263 |
| 7,118,936 B2 * | 10/2006 | Kobayashi et al. | ............. | 438/99 |
| 7,202,412 B2 * | 4/2007 | Yamanaka et al. | ............ | 136/263 |
| 2004/0248394 A1 * | 12/2004 | Kobayashi et al. | ........... | 438/609 |
| 2006/0237059 A1 * | 10/2006 | Kurihara et al. | ............... | 136/263 |
| 2007/0044835 A1 * | 3/2007 | Yoshimoto et al. | ........... | 136/263 |
| 2008/0110496 A1 * | 5/2008 | Jung et al. | ..................... | 136/256 |
| 2009/0216021 A1 * | 8/2009 | Jiang et al. | ..................... | 546/12 |

* cited by examiner

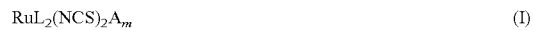

*Primary Examiner* — Peter F Godenschwager
*Assistant Examiner* — M. Reza Asdjodi
(74) *Attorney, Agent, or Firm* — Bacon & Thomas, PLLC

(57) ABSTRACT

The present invention relates to a ruthenium complex and a photoelectric component using the same, and the ruthenium complex is represented by the following formula (I):

$$RuL_2(NCS)_2A_m \qquad (I)$$

wherein L, A and m are defined the same as the specification. The ruthenium complex of the present invention is suitable for Dye-Sensitized Solar Cell (DSSC). Hence, the photoelectric characteristics of the DSSC manufactured with the ruthenium complex of the present invention can be improved.

7 Claims, No Drawings

RUTHENIUM COMPLEX AND PHOTOELECTRIC COMPONENT USING THE SAME

BACKGROUND OF THE INVENTION

1. Field of the Invention

The present invention relates to a ruthenium complex and a photoelectric component using the same and, more particularly, to a ruthenium complex, which is used for the dye-sensitized solar cell (DSSC), and a photoelectric component using the same.

2. Description of Related Art

With the development of industrial technology, the serious problems that the whole world is facing today are the energy crisis and the environmental pollution. In order to solve the global energy crisis and to reduce the environmental pollution, one of the effective means is the solar cell, which can convert the solar energy into the electricity. Since the dye-sensitized solar cell has the advantages of low manufacturing cost, large-scale production, great flexibility, light transmittance, and being capable of use in the buildings, the application of the dye-sensitized solar cell becomes more and more attractive.

Currently, Grätzel et al. have disclosed a series of literatures, for example, O'Regan, B.; Grätzel, M. *Nature* 1991, 353, 737, which show the practicability of the dye-sensitized solar cell. The general structure of the dye-sensitized solar cell comprises an anode, a cathode, a nano-porous titanium dioxide layer, a dye, and electrolyte, wherein the dye plays a critical role in the conversion efficiency of the dye-sensitized solar cell. The dye suitable for the dye-sensitized solar cell must have characteristics in broad absorption spectrum, high molar absorption coefficient, thermal stability, and light stability.

Grätzel's lab has published a serious of ruthenium complexes as the dyes for the dye-sensitized solar cell. Grätzel's lab published a dye-sensitized solar cell prepared with a N3 dye in 1993, and the conversion efficiency of the dye-sensitized solar cell is 10.0% under the illumination of AM 1.5 stimulated light. The incident photon-to-current conversion efficiency (IPCE) value of the N3 dye is 80% in the range of 400 to 600 nm. Although hundreds of dye complexes have developed, the conversion efficiency of those dye complexes is not as good as the N3 dye. The structure of the N3 dye is represented by the following formula (a).

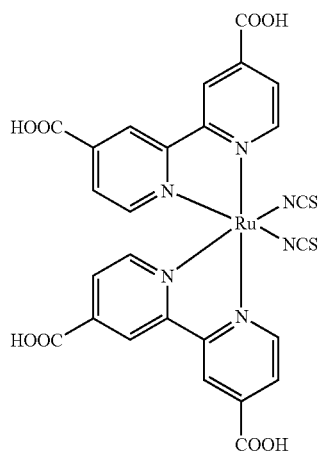

(a)

In 2003, Grätzel's lab published a dye-sensitized solar cell prepared with a N719 dye, and the conversion efficiency of the dye-sensitized solar cell is improved to 10.85% under the illumination of AM 1.5 stimulated light, wherein the structure of the N719 dye is represented by the following formula (b).

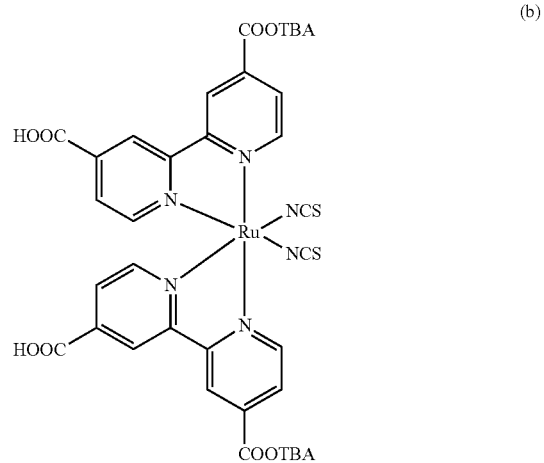

(b)

Grätzel's lab also published a dye-sensitized solar cell prepared with a black dye in 2004, and the conversion efficiency of the dye-sensitized solar cell is 11.04% under the illumination of AM 1.5 stimulated light. The black dye can enhance the spectral response in red and near-IR region, so the conversion efficiency of the dye-sensitized solar cell can be improved. The structure of the black dye is represented by the following formula (c).

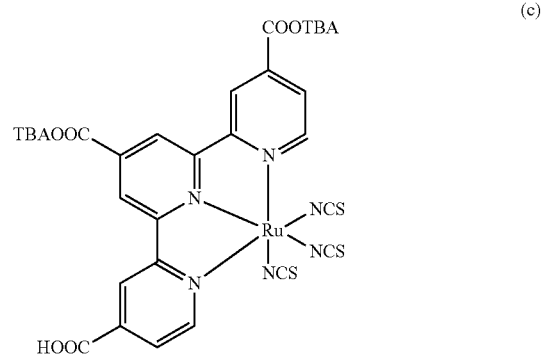

(c)

In addition to the ruthenium complexes such as the N3 dye, the N719 dye, and the black dye, other types of dye compounds, which can be used in the dye-sensitized solar cell, are platinum complexes, osmium complexes, iron complexes, and copper complexes. However, the results of various researches show that the conversion efficiency of the ruthenium complexes is still better than other types of dye compounds.

The dyes for the dye-sensitized solar cell influence the conversion efficiency greatly. Hence, it is desirable to provide a dye compound, which can improve the conversion efficiency of the dye-sensitized solar cell.

SUMMARY OF THE INVENTION

The present invention is to provide a novel ruthenium complex, which is used for a dye-sensitized solar cell to improve the photoelectric efficiency of the dye-sensitized solar cell.

The present invention is also to provide a dye-sensitized solar cell, which has excellent photoelectric property.

Hence, the present invention provides a ruthenium complex, which is represented by the following formula (I):

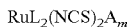

$$RuL_2(NCS)_2A_m \qquad (I)$$

wherein
L is 2,2'-bipyridyl-4,4'-dicarboxylic acid, 2,2'-bipyridyl-4,4'-disulfonic acid, or 2,2'-bipyridyl-4,4'-diphosphonic acid;
A is $N^+R_1R_2R_3R_4$,

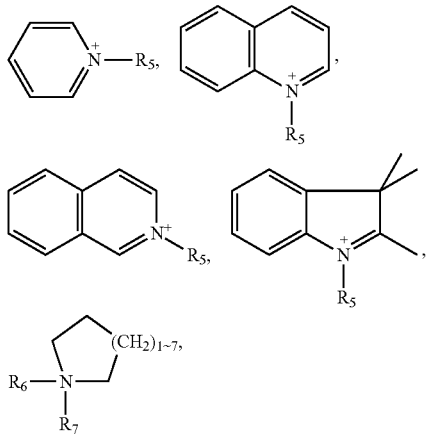

wherein $R_1$ is $C_{5\sim20}$ alkyl, phenyl, or benzyl, $R_2$, $R_3$, and $R_4$ are each independently $C_{1\sim20}$ alkyl, phenyl, or benzyl, $R_5$, $R_6$, and $R_7$ are each independently $C_{1\sim20}$ alkyl; and m is an integral of 1-4.

In the above formula (I), L can be 2,2'-bipyridyl-4,4'-dicarboxylic acid, 2,2'-bipyridyl-4,4'-disulfonic acid, or 2,2'-bipyridyl-4,4'-diphosphonic acid. Preferably, L is 2,2'-bipyridyl-4,4'-dicarboxylic acid.

In the above formula (I), A can be $N^+R_1R_2R_3R_4$,

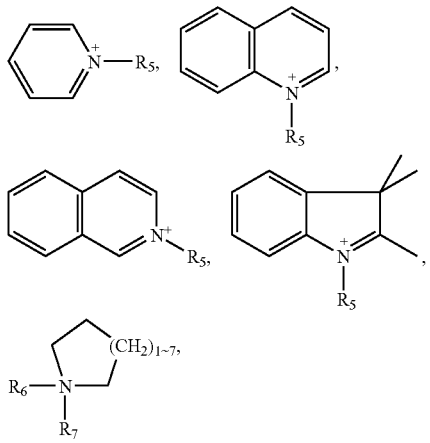

wherein $R_1$ is $C_{5\sim20}$ alkyl, phenyl, or benzyl, $R_2$, $R_3$, and $R_4$ are each independently $C_{1\sim20}$ alkyl, phenyl, or benzyl, $R_5$, $R_6$, and $R_7$ are each independently $C_{1\sim20}$ alkyl. Preferably, A is $N^+R_1R_2R_3R_4$, wherein $R_1$ is $C_{5\sim20}$ alkyl, phenyl, or benzyl, $R_2$, $R_3$, and $R_4$ are each independently $C_{1\sim20}$ alkyl, phenyl, or benzyl. More preferably, A is $N^+R_1R_2R_3R_4$, wherein $R_1$ is $C_{5\sim20}$ alkyl, phenyl, or benzyl, $R_2$, $R_3$, and $R_4$ are each independently $C_{1\sim6}$ alkyl, phenyl, or benzyl. Most preferably, A is $N^+R_1R_2R_3R_4$, wherein $R_1$ is $C_{5\sim20}$ alkyl, phenyl, or benzyl, $R_2$, $R_3$, and $R_4$ are each independently $C_{1\sim6}$ alkyl.

In the above formula (I), m can be an integral of 1-4. Preferably, m is 2, or 3.

The specific examples of ruthenium complex represented by the above formula (I) are:

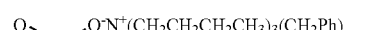

(I-1)

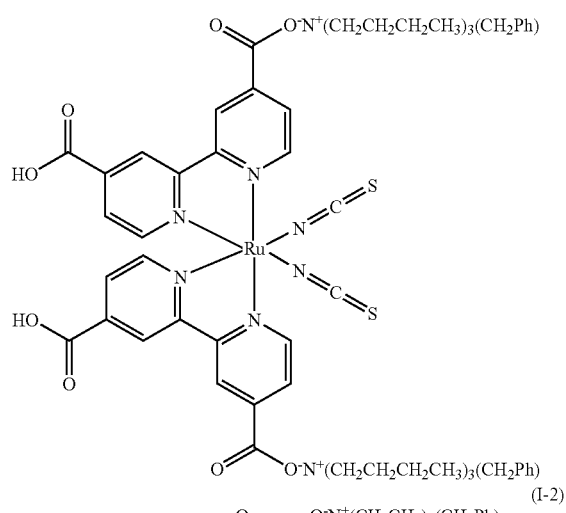

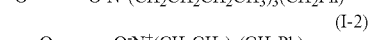

(I-2)

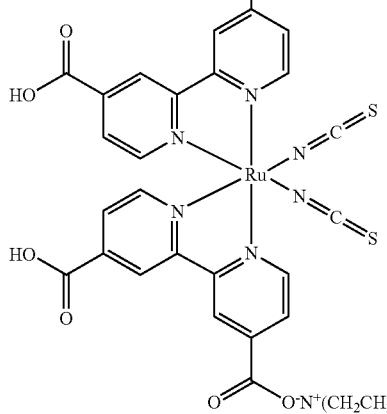

(I-3)

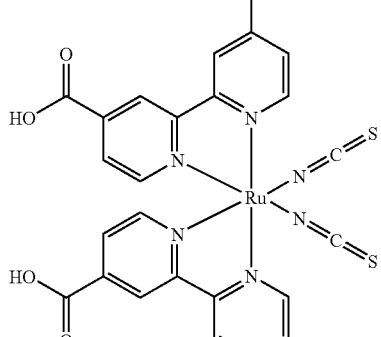

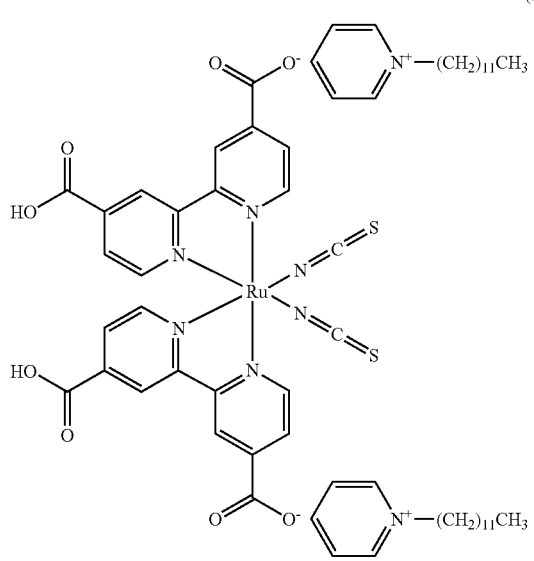
(I-4)
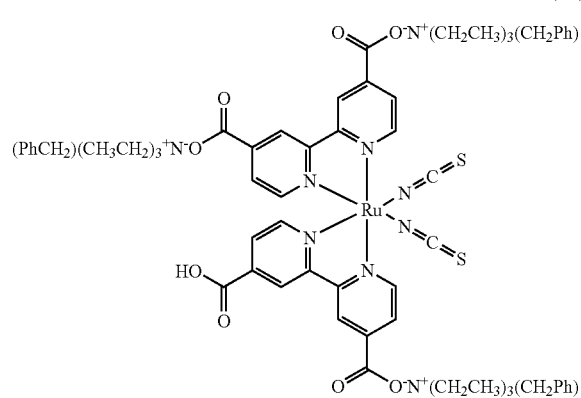
(I-5)
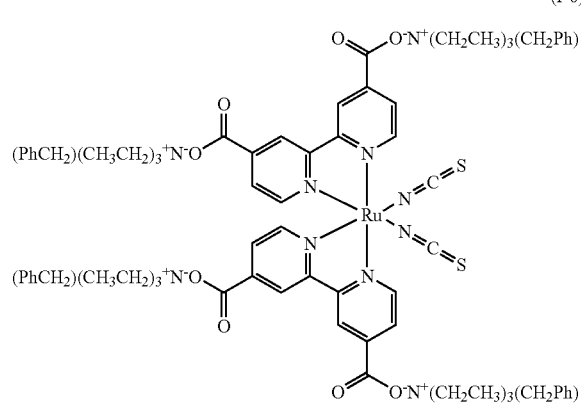
(I-6)
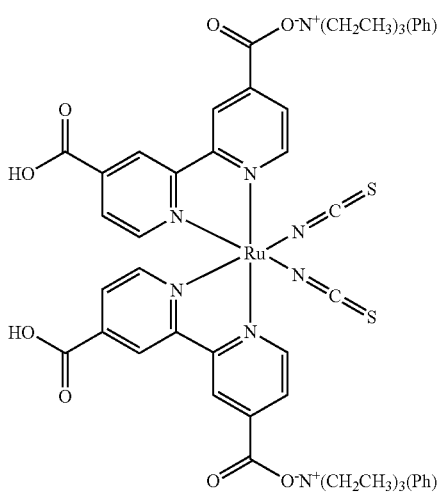
(I-7)
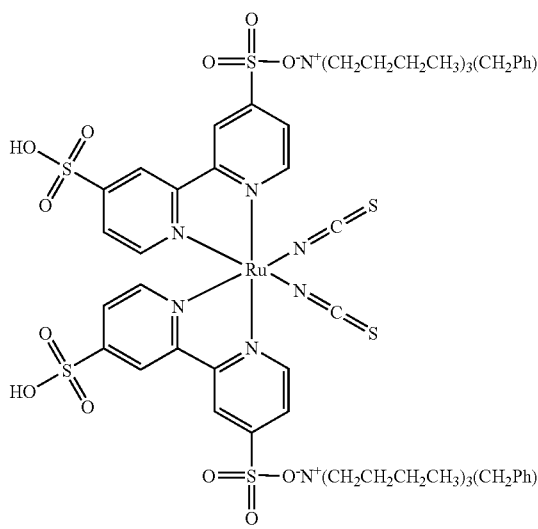
(I-8)
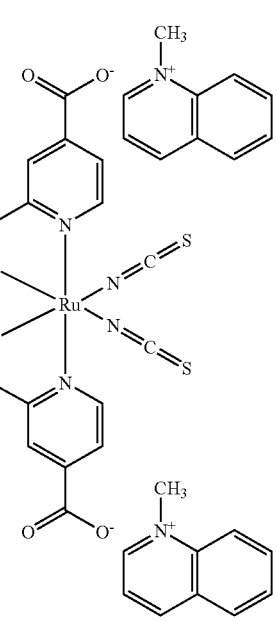
(I-9)

(I-10)

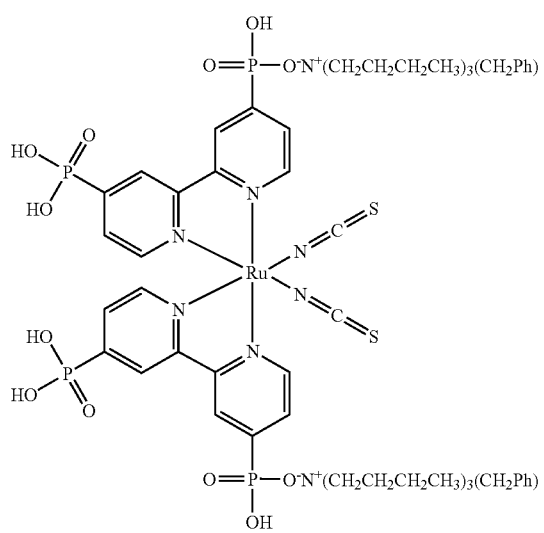

The present invention provides a dye-sensitized solar cell, which comprising the aforementioned ruthenium complex.

In addition, the dye-sensitized solar cell of the present invention comprises: a photoanode, which comprises the aforementioned ruthenium complex; a cathode; and an electrolyte layer disposed between the phoroanode and the cathode.

In the dye-sensitized solar cell of the present invention, the photoanode comprises: a transparent substrate, a transparent conductive layer, a porous semiconductive layer, and a dye of the ruthenium complex.

In the dye-sensitized solar cell of the present invention, the material of the transparent substrate is not particularly limited, as long as the material of the substrate is a transparent material. Preferably, the material of the transparent substrate is a transparent material, which has good moisture resistance, solvent resistance and weather resistance. Thus, the dye-sensitized solar cell can resist moisture or gas from outsides by the transparent substrate. The specific examples of the transparent substrate include, but are not limited to, transparent inorganic substrate, such as quartz and glass; transparent plastic substrate, such as poly(ethylene terephthalate) (PET), poly(ethylene 2,6-naphthalate) (PEN), polycarbonate (PC), polyethylene (PE), polypropylene (PP), and polyimide (PI). Additionally, the thickness of the transparent substrate is not particularly limited, and can be changed according to the transmittance and the demands for the properties of the dye-sensitized solar cell. Preferably, the material of the transparent substrate is glass.

Furthermore, in the dye-sensitized solar cell of the present invention, the material of the transparent conductive layer can be indium tin oxide (ITO), fluorine-doped tin oxide (FTO), ZnO—$Ga_2O_3$, ZnO—$Al_2O_3$, or tin-based oxides.

In addition, in the dye-sensitized solar cell of the present invention, the porous semiconductive layer is made of semiconductor particles. Suitable semiconductor particles may include Si, $TiO_2$, $SnO_2$, ZnO, $WO_3$, $Nb_2O_5$, $TiSrO_3$, and the combination thereof. Preferably, the semiconductor particles are made from $TiO_2$. The average diameter of the semiconductor particles may be 5 to 500 nm. Preferably, the average diameter of the semiconductor particles is 10 to 50 nm. Furthermore, the thickness of the porous semiconductive layer is 5-25 μm.

In the dye-sensitized solar cell of the present invention, the ruthenium complex may be the aforementioned ruthenium complex.

Besides, the material of the cathode for the dye-sensitized solar cell is not particularly limited, and may include any material with conductivity. Otherwise, the material of the cathode can be an insulating material, as long as there is a conductive layer formed on the surface of the cathode, wherein the surface of the cathode is faced to the photoanode. The material of the cathode can be a material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes.

Other objects, advantages, and novel features of the invention will become more apparent from the following detailed description

DETAILED DESCRIPTION OF THE PREFERRED EMBODIMENT

The ruthenium complex of the present invention can be synthesized by the following methods.

cis-di(thiocyanato)-N,N'-bis(2,2'-bipyridyl-4,4'-dicarboxylic acid)ruthenium(II) (N3 dye) is synthesized according to the method described in *Inorganic Chemistry*, Vol. 38, No. 26, 1999, 6298-6305.

cis-di(thiocyanato)-N,N'-bis(2,2'-bipyridyl-4,4'-dicarboxylic acid)ruthenium(II) is dissolved in distilled water, and 10% aqueous solution of benzyltributylammonium hydroxide, which is formulated with 98% benzyltributylammonium chloride reagent (ACROS), is added thereto until the pH value of the reaction solution is 10. Then, the reaction solution is concentrated to obtain a viscous liquid. The viscous liquid is dissolved in methanol, and the diethyl ether is added thereto to precipitate a product. After the wet solid product is dried under vacuum for 1 day, the dried solid product is dissolved in distilled water, and the pH value of the resulted solution is adjusted below 5 with 0.1 M nitric acid$_{(aq)}$. Finally, the ruthenium complex of formula (I-1) is obtained.

The method for manufacturing the dye-sensitized solar cell of the present invention is not particularly limited, and the dye-sensitized solar cell of the present invention can be manufacture by the known methods in the art.

The material of the transparent substrate is not particularly limited, as long as the material of the substrate is a transparent material. Preferably, the material of the transparent substrate is a transparent material, which has good moisture resistance, solvent resistance and weather resistance. Thus, the dye-sensitized solar cell can resist moisture or gas from outsides by the transparent substrate. The specific examples of the transparent substrate include, but are not limited to, transparent inorganic substrate, such as quartz and glass; transparent plastic substrate, such as poly(ethylene terephthalate) (PET), poly(ethylene 2,6-naphthalate) (PEN), polycarbonate (PC), polyethylene (PE), polypropylene (PP), and polyimide (PI). Additionally, the thickness of the transparent substrate is not particularly limited, and can be changed according to the transmittance and the demands for the properties of the dye-sensitized solar cell. In a specific embodiment, the material of the transparent substrate is glass substrate.

Furthermore, the material of the transparent conductive layer can be indium tin oxide (ITO), fluorine-doped tin oxide (FTO), ZnO—Ga$_2$O$_3$, ZnO—Al$_2$O$_3$, or tin-based oxides. In a specific embodiment, fluorine-doped tin oxide is used for transparent conductive layer.

In addition, the porous semiconductive layer is made of semiconductor particles. Suitable semiconductor particles may include Si, TiO$_2$, SnO$_2$, ZnO, WO$_3$, Nb$_2$O$_5$, TiSrO$_3$, and the combination thereof. First, the semiconductor particles are prepared in a form of paste, and then the paste is coated on the transparent conductive substrate. The coating method used herein can be blade coating, spin coating, spry coating, or wetting coating. Additionally, the coating can be held for one time or many times, in order to obtain a porous semiconductive layer with suitable thickness. The semiconductive layer can be a single layer or multiple layers, wherein each layer of the multiple layers is formed by semiconductor particles with different diameters. For example, the semiconductor particles with diameters of 5 to 50 nm is coated in a thickness of 5 to 20 μm, and then the semiconductor particles with diameters of 200 to 400 nm is coated in a thickness of 3 to 5 μm. After drying the resulted product under 50-100° C., the resulted product is sintered under 400-500° C. for 30 min to obtain a multilayer semiconductive layer.

The ruthenium complex can be dissolved in a suitable solvent to prepare a dye solution. Suitable solvents include, but are not limited to, acetonitrile, methanol, ethanol, propyl alcohol, butyl alcohol, dimethyl formamide, and N-methyl-2-pyrrolidinone. Herein, the transparent substrate coated with the semiconductive layer is dipped into a dye solution to make the semiconductive layer absorb the dye in the dye solution completely. After the dye absorption is completed, the transparent substrate coated with the semiconductive layer is taken out and dried. Finally, a photoanode for a dye-sensitized solar cell is obtained.

Besides, the material of the cathode for the dye-sensitized solar cell is not particularly limited, and may include any material with conductivity. Otherwise, the material of the cathode can be an insulating material, as long as there is a conductive layer formed on the surface of the cathode, wherein the surface of the cathode is faced to the photoanode. The material of the cathode can be a material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes. In addition, the liquid electrolyte can be a solution of acetonitrile containing iodine, a solution of N-methyl-2-pyrrolidinone containing iodine, or a solution of 3-methoxy propionitrile containing iodine. In a specific embodiment, the liquid electrolyte can be a solution of acetonitrile containing iodine.

One specific method for manufacturing the dye-sensitized solar cell of the present invention is presented as follow.

First, a paste containing TiO$_2$ particles with diameter of 20~30 nm is coated on a glass substrate covered with fluorine-doped tin oxide (FTO) for one time or several times. Then, the resulted glass substrate is sintered under 450° C. for 30 min.

The ruthenium complex is dissolved in a mixture of acetonitrile and t-butanol (1:1 v/v) to formulate a dye solution of ruthenium complex. Then, the aforementioned glass substrate with porous TiO$_2$ layer is dipped into the dye solution. After the porous TiO$_2$ layer absorbs the dye in the dye solution, the resulted glass substrate is taken out and dried. Finally, a photoanode is obtained.

A glass substrate covered with fluorine-doped tin oxide is drilled to form an inlet with diameter of 0.75 μm, wherein the inlet is used for injecting the electrolyte. Then, a solution of H$_2$PtCl$_6$ is coated on the glass substrate covered with fluorine-doped tin oxide, and the glass substrate is heated to 400° C. for 15 min. Finally, a cathode is obtained.

Sequentially, a thermoplastic polymer layer with a thickness of 60 μm is disposed between the photoanode and the cathode. These two electrodes are pressed under 120 to 140° C. to adhere with each other.

Then, an electrolyte is injected, wherein the electrolyte is a solution of acetonitrile containing 0.03 M I$_2$/0.3 M LiI/0.5 M t-butyl-pyridine. After the inlet is sealed with thermoplastic polymer layer, a dye-sensitized solar cell of the present invention is obtained.

The following examples are intended for the purpose of illustration of the present invention. However, the scope of the present invention should be defined as the claims appended hereto, and the following examples should not be construed as in any way limiting the scope of the present invention. Without specific explanations, the unit of the parts and percentages used in the examples is calculated by weight, and the temperature is represented by Celsius degrees (° C.). The relation between the parts by weight and the parts by volume is just like the relation between kilogram and liter.

Example 1

Synthesis of cis-di(thiocyanato)-N,N'-bis(2,2'-bipyridyl-4,4'-dicarboxylic acid)ruthenium(II)bis(benzyltributylammonium) (I-1)

0.50 parts of cis-di(thiocyanato)-N,N'-bis(2,2'-bipyridyl-4,4'-dicarboxylic acid)ruthenium(II) (N3 dye), which was prepared according to the method described in *Inorganic Chemistry*, Vol. 38, No. 26, 1999, 6298-6305, and 10 parts of distilled water were added into a reaction flask, and the reaction solution was stirred. Then, 10% aqueous solution of benzyltributylammonium hydroxide, which was formulated with 98% benzyltributylammonium chloride reagent (ACROS), was added into the reaction solution drop by drop, until the pH value of the reaction solution was 10. The rotary-evaporator was used for removing the solvent from the reaction solution to obtain a viscous liquid. The viscous liquid was dissolved in methanol, diethyl ether was added thereto to obtain a precipitate, and the wet solid precipitate was taken out and dried under vacuum for 1 day. The dried solid was dissolved in 10 parts of distilled water, and 0.1 M nitric acid$_{(aq)}$ was used to adjust the pH value of the resulted solution under 5. The sintered glass filter was used for filtering the product out, and 5 parts of distilled water with pH 4.1 was used for washing the product. Finally, 0.52 parts of black solid product (I-1) was obtained, and the yield of the product (I-1) was 61.5%.

Example 2

Synthesis of cis-di(thiocyanato)-N,N'-bis(2,2'-bipyridyl-4,4'-dicarboxylic acid)ruthenium(II)bis(benzyltriethylammonium)(I-2)

The process for preparing the compound of the present example is the same as that described in Example 1, except that a solution of benzyltributylammonium hydroxide is substituted with a solution of benzyltriethylammonium hydroxide (TCI Co., Ltd.). Here, 0.30 parts of black solid product (I-2) was obtained, and the yield of the product (I-2) was 41.1%.

Example 3

Synthesis of cis-di(thiocyanato)-N,N'-bis(2,2'-bipyridyl-4,4'-dicarboxylic acid)ruthenium(II)bis(triethylhexylammonium) (I-3)

0.50 parts of cis-di(thiocyanato)-N,N'-bis(2,2'-bipyridyl-4,4'-dicarboxylic acid)ruthenium(II) (N3 dye), and 10 parts of distilled water were added into a reaction flask, and the reaction solution was stirred. Then, 10% aqueous solution of triethylhexylammonium hydroxide, which was formulated with 99% triethylhexylammonium bromide reagent (ALDRICH), was added into the reaction solution drop by drop, until the pH value of the reaction solution was 12. The rotary-evaporator was used for removing the solvent from the reaction solution to obtain a viscous liquid. The viscous liquid was dissolved in methanol, diethyl ether was added thereto to obtain a precipitate, and the wet solid precipitate was taken out and dried under vacuum for 1 day. The dried solid was dissolved in 10 parts of distilled water, and 0.1 M nitric acid$_{(aq)}$ was used to adjust the pH value of the resulted solution under 4. The sintered glass filter was used for filtering the product out, and 5 parts of distilled water with pH 4.1 was used for washing the product. Finally, 0.44 parts of black solid product (I-3) was obtained, and the yield of the product (I-3) was 81.5%.

Example 4

Synthesis of cis-di(thiocyanato)-N,N'-bis(2,2'-bipyridyl-4,4'-dicarboxylic acid)ruthenium(II)bis(1-dodecylpyridinium) (I-4)

The process for preparing the compound of the present example is the same as that described in Example 3, except that a solution of triethylhexylammonium hydroxide is substituted with a solution of 1-dodecylpyridinium hydroxide, which is formulated with 98% 1-dodecylpyridinium chloride reagent (ALDRICH). Here, 0.20 parts of black solid product (I-4) was obtained, and the yield of the product (I-4) was 32.8%.

Example 5

Synthesis of cis-di(thiocyanato)-N,N'-bis(2,2'-bipyridyl-4,4'-dicarboxylic acid)ruthenium(II)tris(benzyltriethylammonium) (I-5)

0.20 parts of benzyltriethylammonium hydroxide, and 100 parts of methanol were added into a reaction flask, and the reaction solution was stirred. Then, 0.10 parts of cis-di(thiocyanato)-N,N'-bis(2,2'-bipyridyl-4,4'-dicarboxylic acid)ruthenium(II)bis(benzyltriethylammonium) (I-2) was added into the reaction solution, and the reaction solution was stirred and reacted for 2.5 hrs. The rotary-evaporator was used for removing the solvent from the reaction solution, and the product was precipitated from the reaction solution. The sintered glass filter was used for filtering the product out, and 10 parts of distilled water was used for washing the product. Finally, 0.08 parts of black solid product (I-5) was obtained, and the yield of the product (I-5) was 74.0%.

Example 6

Synthesis of cis-di(thiocyanato)-N,N'-bis(2,2'-bipyridyl-4,4'-dicarboxylic acid)ruthenium(II) tetrakis(benzyltriethylammonium) (I-6)

0.50 parts of cis-di(thiocyanato)-N,N'-bis(2,2'-bipyridyl-4,4'-dicarboxylic acid)ruthenium(II), and 50 parts of distilled water were added into a reaction flask, and the reaction solution was stirred. Then, 10% aqueous solution of benzyltriethylammonium hydroxide was added into the reaction solution drop by drop, until the pH value of the reaction solution was 7. The rotary-evaporator was used for removing the solvent from the reaction solution to obtain a viscous liquid. The viscous liquid was dissolved in methanol, diethyl ether was added thereto to obtain a precipitate, and the wet solid precipitate was taken out and dried under vacuum for 1 day. Finally, 0.43 parts of black solid product (I-6) was obtained, and the yield of the product (I-6) was 68.0%.

Example 7

Preparation of a Dye-Sensitized Solar Cell

A paste containing $TiO_2$ particles with diameter of 20~30 nm was coated on a glass substrate covered with fluorine-doped tin oxide (FTO) for one time or several times, wherein the thickness of the glass substrate was 4 mm and the electric resistance of the glass substrate is 10Ω/□. Then, the resulted glass substrate was sintered under 450° C. for 30 min, and the thickness of the sintered porous $TiO_2$ layer was 10 to 12 μm.

The ruthenium complex prepared by Example 1 was dissolved in a mixture of acetonitrile and t-butanol (1:1 v/v), and a dye solution with 0.5 mM ruthenium complex was prepared. Then, the aforementioned glass substrate covered with porous $TiO_2$ layer was dipped into the dye solution to make the dye adhere on the porous $TiO_2$ layer. After 16 to 24 hours, the resulted glass substrate was taken out and dried, and then a photoanode was obtained.

A glass substrate covered with fluorine-doped tin oxide was drilled to form an inlet with diameter of 0.75 μm, wherein the inlet was used for injecting the electrolyte. Then, a solution of $H_2PtCl_6$ (2 mg Pt in 1 ml ethanol) was coated on the glass substrate covered with fluorine-doped tin oxide, and the glass substrate was heated to 400° C. for 15 min. Finally, a cathode was obtained.

Sequentially, a thermoplastic polymer layer with a thickness of 60 μm was disposed between the photoanode and the cathode. These two electrodes were pressed under 120 to 140° C. to adhere with each other.

Then, an electrolyte was injected, wherein the electrolyte was a solution of acetonitrile containing 0.03 M $I_2$/0.3 M LiI/0.5 M t-butyl-pyridine. After the inlet was sealed with thermoplastic polymer layer, a dye-sensitized solar cell of the present example was obtained.

Example 8

Preparation of a Dye-Sensitized Solar Cell

The process for preparing the dye-sensitized solar cell of the present example is the same as that described in Example 7, except that the ruthenium complex prepared by Example 1 is substituted with the ruthenium complex prepared by Example 2.

Example 9

Preparation of a Dye-Sensitized Solar Cell

The process for preparing the dye-sensitized solar cell of the present example is the same as that described in Example 7, except that the ruthenium complex prepared by Example 1 is substituted with the ruthenium complex prepared by Example 3.

Example 10

Preparation of a Dye-Sensitized Solar Cell

The process for preparing the dye-sensitized solar cell of the present example is the same as that described in Example 7, except that the ruthenium complex prepared by Example 1 is substituted with the ruthenium complex prepared by Example 4.

Example 11

Preparation of a Dye-Sensitized Solar Cell

The process for preparing the dye-sensitized solar cell of the present example is the same as that described in Example 7, except that the ruthenium complex prepared by Example 1 is substituted with the ruthenium complex prepared by Example 5.

Example 12

Preparation of a Dye-Sensitized Solar Cell

The process for preparing the dye-sensitized solar cell of the present example is the same as that described in Example 7, except that the ruthenium complex prepared by Example 1 is substituted with the ruthenium complex prepared by Example 6.

Comparative Example

The process for preparing the dye-sensitized solar cell of the present example is the same as that described in Example 7, except that the ruthenium complex prepared by Example 1 is substituted with N719.

Testing Method and Results
Test for the Photoelectric Characteristics

The short circuit current ($J_{SC}$), open circuit voltage ($V_{OC}$), filling factor (FF), photoelectric conversion efficiency ($\eta$), and incident photon-to-current conversion efficiency (IPCE) of the dye-sensitized solar cells prepared by Examples 7-12 and Comparative Example were measured under the illumination of AM 1.5 stimulated light. The testing results are shown in the following Table 1:

TABLE 1

Testing results of the dye and the dye-sensitized solar cell

| | dye | $J_{SC}$ (mA/cm$^2$) | $V_{OC}$ (V) | FF | $\eta$ (%) |
|---|---|---|---|---|---|
| Example 7 | I-1 | 8.22 | 0.78 | 0.64 | 4.09 |
| Example 8 | I-2 | 9.42 | 0.79 | 0.62 | 4.54 |
| Example 9 | I-3 | 8.46 | 0.80 | 0.64 | 4.33 |
| Example 10 | I-4 | 6.98 | 0.68 | 0.63 | 3.00 |
| Example 11 | I-5 | 7.84 | 0.81 | 0.65 | 4.12 |
| Example 12 | I-6 | 7.99 | 0.75 | 0.62 | 3.74 |
| Comparative Example | N719 | 7.36 | 0.76 | 0.61 | 3.38 |

The resting results of Table 1 show that the short circuit current ($J_{SC}$), the open circuit voltage ($V_{OC}$) and the filling factor (FF) of the dye-sensitized solar cells prepared by the ruthenium complex of the present invention are improved, as compared with the dye-sensitized solar cell prepared by the N719 dye. It means that the ruthenium complex of the present invention can improve the photoelectric characteristics of the dye-sensitized solar cell.

In conclusion, the present invention is different from the prior arts in several ways, such as in purposes, methods and efficiency, or even in technology and research and design. Although the present invention has been explained in relation to its preferred embodiment, it is to be understood that many other possible modifications and variations can be made without departing from the scope of the invention as hereinafter claimed. Hence, the scope of the present invention should be defined as the claims appended hereto, and the foregoing examples should not be construed as in any way limiting the scope of the present invention.

What is claimed is:

1. A ruthenium complex, which is represented by the following formula (I):

$$RuL_2(NCS)_2A_m \qquad (I)$$

wherein
L is 2,2'-bipyridyl-4,4'-dicarboxylic acid;
A is $N^+R_1R_2R_3R_4$,
 wherein $R_1$ is benzyl, $R_2$, $R_3$, and $R_4$ are each independently $C_{1\sim20}$ alkyl, phenyl, or benzyl;
m is 2, 3, or 4; and
all A are the same.

2. The ruthenium complex as claimed in claim 1, wherein A is $N^+R_1R_2R_3R_4$, $R_1$ is benzyl, $R_2$, $R_3$, and $R_4$ are each independently $C_{1\sim6}$ alkyl.

3. The ruthenium complex as claimed in claim 1, wherein the ruthenium complex is a dye compound for a dye-sensitized solar cell.

4. The ruthenium complex as claimed in claim 1, wherein formula (I) is the following formula (I-2):

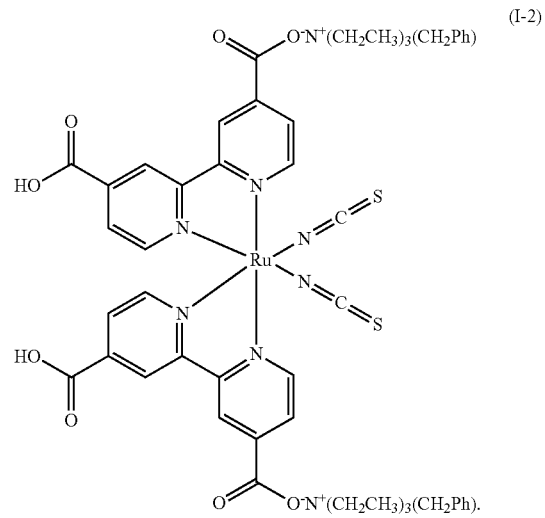

5. The ruthenium complex as claimed in claim 4, wherein the ruthenium complex is a dye compound for a dye-sensitized solar cell.

6. A dye-sensitized solar cell, comprising:
 (a) a photoanode, which comprises a ruthenium complex represented by the following formula (I):

$$RuL_2(NCS)_2A_m \qquad (I)$$

wherein
L is 2,2'-bipyridyl-4,4'-dicarboxylic acid;
A is $N^+R_1R_2R_3R_4$, wherein $R_1$ is benzyl, $R_2$, $R_3$, and $R_4$ are each independently $C_{1\sim20}$alkyl, phenyl, or benzyl;
m is 2, 3, or 4; and
all A are the same;
  (b) a cathode; and
  (c) an electrolyte layer disposed between the photoanode and the cathode.

7. A dye solution, comprising:
(A) a ruthenium complex represented by the following formula (I), wherein the content of the ruthenium is 0.01-1 wt %:

$$RuL_2(NCS)_2A_m \qquad (I)$$

wherein
L is 2,2'-bipyridyl-4,4'-dicarboxylic acid;
A is $N^+R_1R_2R_3R_4$,
wherein $R_1$ is benzyl, $R_2$, $R_3$, and $R_4$ are each independently $C_{1\sim20}$alkyl, phenyl, or benzyl;
m is 2, 3, or 4; and
all A are the same;
  (B) an organic solvent, wherein the content of the organic solvent is 99.99-99 wt %, and the organic solvent is selected from the group consisting of acetonitrile, methanol, ethanol, propyl alcohol, butyl alcohol, dimethyl formamide, and N-methyl-2-pyrrolidinone.

* * * * *